United States Patent
Zhao et al.

(10) Patent No.: US 8,162,480 B2
(45) Date of Patent: *Apr. 24, 2012

(54) SYSTEMS AND SOFTWARE FOR WAVEFRONT DATA PROCESSING, VISION CORRECTION, AND OTHER APPLICATIONS

(75) Inventors: Huawei Zhao, Irvine, CA (US); Li Chen, Santa Clara, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/650,130

(22) Filed: Dec. 30, 2009

(65) Prior Publication Data

US 2010/0103378 A1 Apr. 29, 2010

Related U.S. Application Data

(63) Continuation of application No. 12/263,433, filed on Oct. 31, 2008, now Pat. No. 7,654,672.

(60) Provisional application No. 60/984,355, filed on Oct. 31, 2007, provisional application No. 61/028,890, filed on Feb. 14, 2008.

(51) Int. Cl.
*A61B 3/10* (2006.01)

(52) U.S. Cl. ........................ 351/221; 351/205

(58) Field of Classification Search ........... 351/200–246
See application file for complete search history.

(56) References Cited

U.S. PATENT DOCUMENTS

| | | | |
|---|---|---|---|
| 6,050,687 A * | 4/2000 | Bille et al. | 351/212 |
| 6,588,900 B1 | 7/2003 | Le Gargasson et al. | 351/200 |
| 6,609,793 B2 | 8/2003 | Norrby et al. | 351/205 |
| 6,809,793 B1 | 10/2004 | Phan et al. | 355/30 |
| 6,830,332 B2 | 12/2004 | Piers et al. | 351/159 |
| 6,964,659 B2 | 11/2005 | Gross et al. | 606/5 |
| 7,654,672 B2 * | 2/2010 | Zhao et al. | 351/221 |
| 7,771,053 B2 * | 8/2010 | Polland et al. | 351/246 |
| 2003/0112411 A1 * | 6/2003 | Martino | 351/212 |
| 2005/0105044 A1 | 5/2005 | Warden et al. | 351/159 |
| 2008/0074614 A1 * | 3/2008 | Leblanc et al. | 351/205 |

FOREIGN PATENT DOCUMENTS
WO WO-03060568 A2 7/2003

OTHER PUBLICATIONS

Liang J. et al., "Objective measurement of wave aberrations of the human eye with the use of a Hartmann-Shack wave-front sensor," J Opt Soc Am A Opt Image Sci Vis, 1994, 11 (7), 1949-1957.

* cited by examiner

*Primary Examiner* — Mohammed Hasan
(74) *Attorney, Agent, or Firm* — Abbott Medical Optics Inc.

(57) ABSTRACT

A system for providing vision contains an aberrometer, a wavefront sensor, and a transfer optical system. The aberrometer is configured to measure a received wavefront. The aberrometer includes a wavefront sensor and a transfer optical system for transferring an input wavefront so as to the provide the received wavefront at or near the wavefront sensor. The system also includes a processor in communication with the aberrometer, a readable memory, and instructions located within the memory. The readable memory contains one or more system error parameters and instructions for calculating the input wavefront based on the received wavefront and the one or more system error parameters.

10 Claims, 2 Drawing Sheets

SYSTEMS AND SOFTWARE FOR WAVEFRONT DATA PROCESSING, VISION CORRECTION, AND OTHER APPLICATIONS

RELATED APPLICATION

This application is a continuation application of, and claims prior to, U.S. patent application Ser. No. 12/263,433, filed Oct. 31, 2008, now U.S. Pat. No. 7,654,672 B2 which claims priority under 35 U.S.C §119(e) to provisional application No. 60/984,355, filed on Oct. 31, 2007 and provisional application No. 61/028,890, filed on Feb. 14, 2008, the entire contents of each of which applications are hereby incorporated by reference in their entirety for all purposes as if fully set forth herein.

BACKGROUND OF THE INVENTION

1. Field of the Invention

The present invention relates generally to systems and software for determining aberrations, and more specifically to systems and software for determining aberrations of an input wavefront by correcting for, compensating for, or reducing system errors.

2. Description of the Related Art

Wavefront imaging system may be generally considered to be systems for transferring optical information contained in an object or input wavefront from an object space to an image space containing an image or output wavefront generally located at an image plane. A wavefront sensor, containing a detector or detector array such as a CCD or CMOS detector array, is generally placed at or near an image plane within the image space in order to provide one or more electronic or digital images of the image wavefront. The wavefront sensor may include additional optics disposed at or near the image space to further transfer or process the image wavefront. For example, a lenslet array may be disposed at or near the image plane in order to sample various portions the image wavefront. In some cases, a recording media such as a holographic plate and a reference beam may be provided to record the wavefront for later reconstruction. In any case, the recorded information in the image plane or space is generally used to provide information contained in the original object wavefront.

The transfer of optical information by the wavefront imaging system to the wavefront sensor is, however, generally imperfect. At a minimum, the effects of diffraction, which arise from the use of a finite system aperture, will limit the ability of the wavefront imaging system to transfer information contained in the object space to the conjugate image space. In addition, the wavefront imaging system will produce other errors or aberrations during the transfer process, for example, aberrations produced by imperfect optical elements within the system and/or misalignment between these optical elements.

In prior art wavefront imaging systems, aberrations or errors of the imaging system are typically not accounted for, which can lead to errors in accurately determining aberrations of an input wavefront, which has passed through an aberrated imaging system, based on measurements of an output wavefront. Rather, the imaging system is designed so as to minimize system optical aberrations, and is carefully aligned to reduce alignment errors. However, the inventor have found that even relatively small system aberrations or misalignment can lead to large errors in calculating the magnitude of higher order aberration terms of the original input wavefront.

In some cases, the errors or aberrations produced by the optical imaging system may depend, not only on the system aberrations themselves, but also on the aberrations contained in the original input wavefront.

Accordingly, better methods and systems are needed to provide more accurate calculation of the aberrations contained in an input wavefront after it has passed through a wavefront imaging system containing system aberrations and misalignments.

BRIEF DESCRIPTION OF THE DRAWINGS

Embodiments of the present invention may be better understood from the following detailed description when read in conjunction with the accompanying drawings. Such embodiments, which are for illustrative purposes only, depict novel and non-obvious aspects of the invention. The drawings include the following figures.

DETAILED DESCRIPTION

Embodiments of the present invention are generally directed to systems and software for measuring or determining aberrations of an input wavefront based on an output wavefront produced when the input wavefront passes through an imaging system that produces an output wavefront that is received by a wavefront sensor. The measurement or determination of the input wavefront is provided by correcting for, compensating for, or reducing system errors and/or input wavefront errors that may alter the error produced by the system. Embodiments of the present invention will be illustrated using aberrometer systems used in the area of ophthalmic measurement and correction. However, it will be understood that embodiments of the present invention may be utilized in other optical applications where measurement of a wavefront or image may be affected by transfer of the wavefront or image through a transfer optical system.

Figure 1:
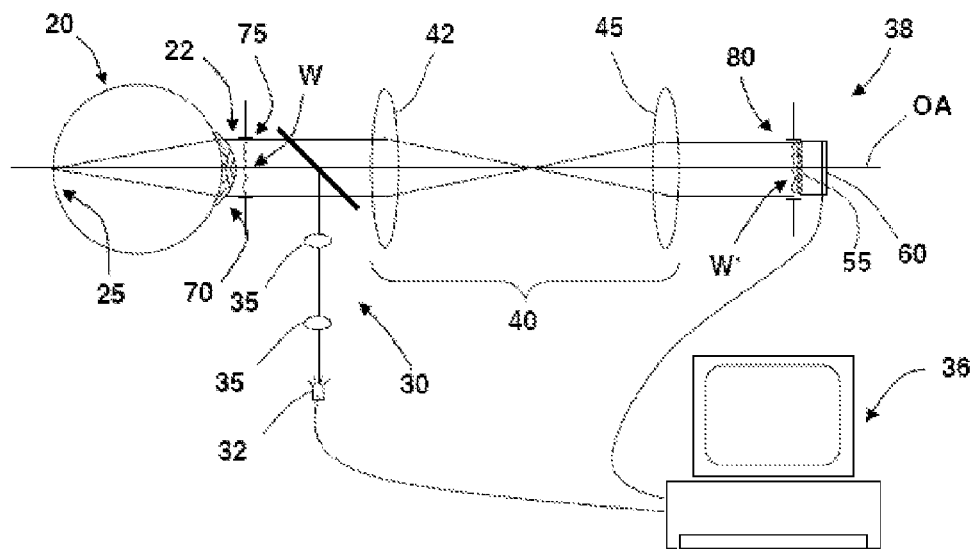
FIG. 1 is a schematic drawing of a wavefront sensor according to an embodiment of the present invention.

Referring to FIG. 1, in certain embodiments of the present invention, an aberrometer or wavefront measurement system 10 is configured to provide a characterization of an input or object wavefront W of a subject eye 20 containing a cornea 22 and a retina 25. The wavefront measurement system 10 comprises an illumination optical system 30 that includes an illumination source 32 and may include one or more lenses 35 or other optical elements that are configured to direct light from the light source 32 to the eye 20 and to preferably focus the light onto the retina 25. The wavefront measurement system 10 also includes a computer or processor 36 that is used to control various components of the system 10, to collect input data from the system 10, and to make calculations regarding aberrations of the wavefronts W and/or W', aberrations of the system 10, and/or aberrations of the eye 20. The wavefront measurement system 10 also comprises an optical relay or image relay system 40 that is configured to receive and relay an input wavefront W from the eye 20. The input wavefront W is transformed by the relay system or telescope 40 into a wavefront W' that is received by a wavefront sensor 38.

In certain embodiments, the optical relay system 40 comprises a first lens 42 and a second lens 45. As the input wavefront W passes through the first lens 42 of relay system 40, light is generally directed or focused onto an internal focal plane. This light then passes through the second lens 45 to form the wavefront W', which is received by the wavefront sensor 38. Some embodiments, at least one of the lenses 42, 45 may be replaced or supplemented by another optical element, for example, a diffractive optical element (DOE) or mirror. In general, aberrations may be introduced into the wavefront W' that were not present in the input wavefront W, for example, by misalignment between the lenses 42, 45 in translation (dx, dy, dz) or rotation (dθx, dθy, dθz). Alternatively or additionally, aberrations may be introduced due to inherent optical characteristics of the optical relay system 40, for example, spherical aberrations introduced through the use of spherical lenses.

In the illustrated embodiment, the wavefront sensor 38 is a Shack-Hartmann wavefront sensor comprising a lenslet array 55 and a detector 60, which may be a CCD, CMOS, or similar type detector comprising an array of pixel elements. Alternatively, other types of wavefront sensors may be used, for example, an interferometer or phase diversity sensor arrangement. In the illustrated embodiment shown in FIG. 2, the test object is an eye 70 which produces the wavefront W at an exit pupil 75. The wavefront W is produced by focused light reflected by the eyes retina that passes through the eye. In such embodiments, a mathematical relationship may be built of the wavefront aberrations in between the entrance pupil of the eye and the exit pupil of the relay system using Fourier polynomials and Zernike polynomials. In certain embodiments, the wavefront W also includes aberrations as it passes from the cornea of the eye to the pupil 75, which may be included in the aberrations calculated for the transferred wavefront W'. In other embodiments, aberrations introduced into the wavefront sensor 50 may also be included in the wavefront analysis.

In some embodiments, more than one relay system may be disposed between the test object and the wavefront sensor 50, in which case an analysis according to embodiments of the present invention may be used to calculate aberrations introduced into the wavefront from the test object.

In certain embodiments, the computer or processor 36 contains memory including instructions for calculating aberrations of the wavefront W', for example, by representing the wavefront W' as a polynomial, such as a Zernike polynomial or Fourier polynomial, for example as taught in U.S. Pat. Nos. 6,609,793, 6,830,332, which are incorporated by reference in their entirety. The computer 36 may be a desktop or portable computer. Alternatively, the computer 36 may be incorporated into an electronic circuit board or chip containing on-board memory or in communications with separate external memory.

In some embodiments, a memory for the computer 36 contains value for certain parameters. For example, the memory may contain one or more system error parameters. For example, the system error parameters may include errors, aberrations, or misalignment information regarding the wavefront measurement system 10 and/or the optical relay system 40. The system error parameters may include coefficients of a polynomial equation representing an error or aberration, such as Zernike polynomial, a Taylor polynomial, or the like.

Figure 3:
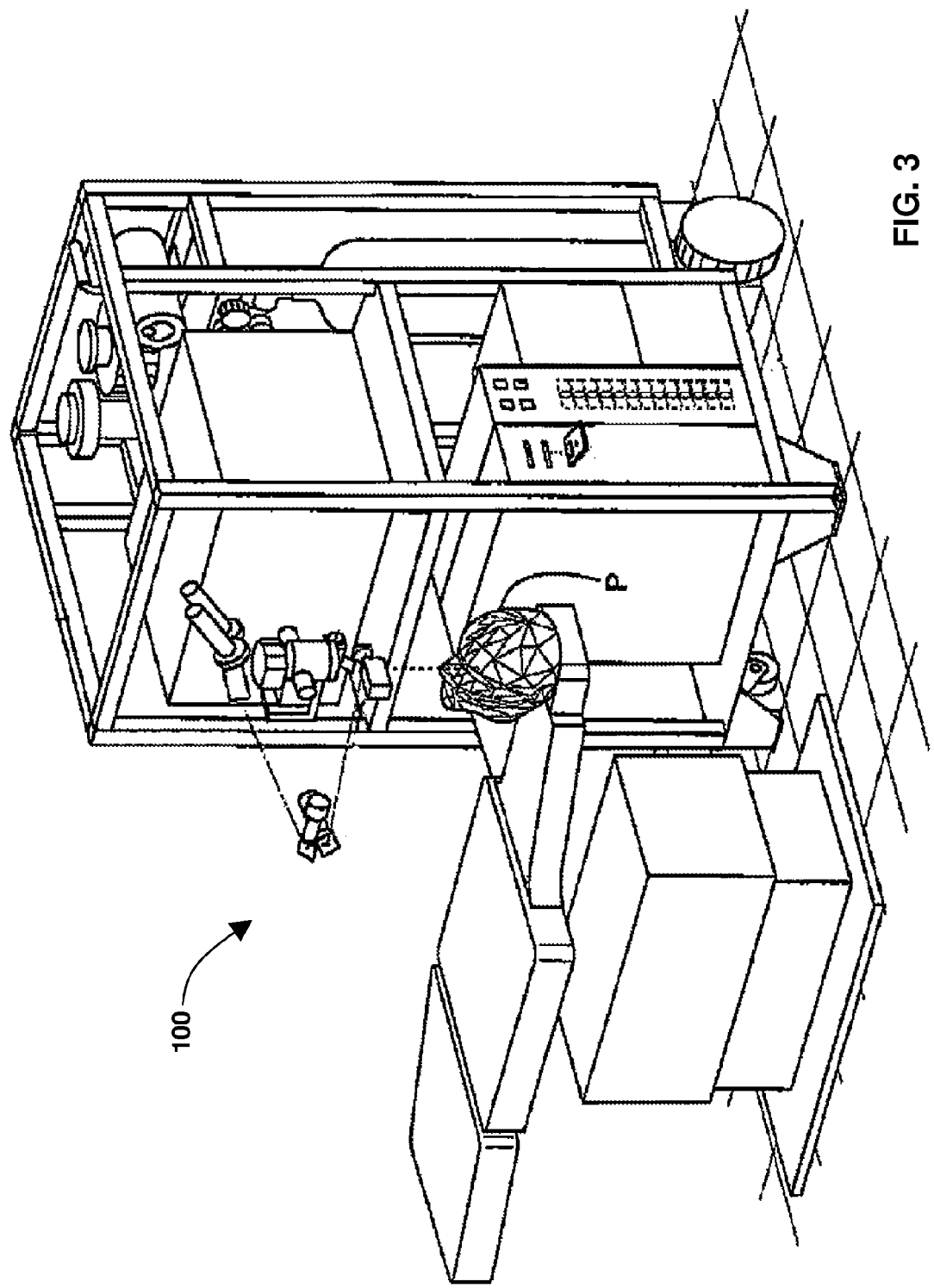
FIG. 3 is system for performing a corneal ablation surgery according to an embodiment of the present invention.

Referring to FIG. 3, in certain embodiments, a corneal refractive surgical system 100 includes a laser for performing a corneal refractive surgery such as a LASIK or PRK procedure, for example, as disclosed in U.S. Pat. No. 6,964,659, which is herein incorporated by reference in its entirety. The surgical system 100 is provided with a treatment profile for a cornea based on the wavefront W' that is calculated based on the wavefront W and corrections or compensations for the transfer system 40 and/or cross-terms of the transfer system and the input wavefront W in accordance to embodiments discussed herein, or the like.

In some embodiments, a method or formulas are used in wavefront measurements using a confocal system from one point (pin hole or small aperture) to another conjugated point (pin hole or small aperture) instead of from one plane to another plane. In other embodiments, a method may be applied for any other aerometer or device to measure accurately the aberrations of human eye or other optical system that uses a relay system before the wavefront sensor.

In certain embodiments, the aberrations introduced into the object wavefront W may reduced or eliminated by adjusted, supplementing, or replacing optical elements of the relay system 40 or some other optical element of the measurement system 10. In some embodiments, the final design of a wavefront measurement system or relay system 10 may be adjusted to reduce or eliminate the sensitivity to misalignment of certain optical elements of the system.

In some embodiments, a wavefront propagation theory may be used to derive mathematical expressions of the wavefront propagation through the optical relay system 40. The basis for the wavefront propagation may be based on:
  Fresnel-Kirchhoff theory
  Distribution and phase function
  Fourier optics
In such embodiments, the wavefront transfer function or matrix may be given by:

$$W'(x,y) = WTF(x,y) * W(x,y) \tag{1}$$

$$[W'] = [WTF] * [W] \tag{2}$$

W, WTF, W' may use sets of polynomials

Additionally or alternatively, ray tracing simulations may be used to derive mathematical expressions of the wavefront propagation through the optical relay system 40, as discussed in further detail below.

The Fresnel-Kirchhoff's approximate formula may include the following relations:

$$g(x_0, y_0) = g_0(x_0, y_0) \exp[-jkW(x_0, y_0)] \tag{3}$$

where
- $g_0(x_0, y_0)$ is the ideal pupil function;
- $W(x_0, y_0)$ is the ideal pupil function;
- $k = \dfrac{2\pi}{\lambda}$ where $\lambda$ is the wavelength;

$$u(x_i, y_i) = \frac{1}{j\lambda} \int_{-\infty}^{+\infty} \int g(x_0, y_0) \frac{\exp(jkr)}{r} dx_0 dy_0 \tag{4}$$

where $$r = \sqrt{z_i^2 + (x_i - x_0)^2 + (y_i - y_0)^2}$$

$$r = \sqrt{z_i^2 + (x_i - x_0)^2 + (y_i - y_0)^2}$$

$$\cong \left\{ z_i + \frac{(x_i - x_0)^2 + (y_i - y_0)^2}{2z_i} - \frac{[(x_i - x_0)^2 + (y_i - y_0)^2]^2}{8z_i^3} \ldots \right\} \Rightarrow \tag{5}$$

CloseField $$\cong \left\{ z_i + \frac{(x_i - x_0)^2 + (y_i - y_0)^2}{2z_i} \right\} \Rightarrow \text{Fresnel}$$

or $$\cong \left\{ z_i + \frac{x_i^2 + y_i^2}{2z_i} - \frac{x_i x_0 + y_i y_0}{z_i} \right\} \Rightarrow \text{Fraunhofer}$$

Embodiments of the present invention generally relate to optical imaging systems and methods of determining the image errors produced by such optical imaging systems. Embodiments of the present invention discussed below are for illustrative purposes and are not intended to limit the scope of the present invention. Aspects of the present invention are discussed below in conjunction with the "Slides" referenced therein and include with this disclosure.

As discussed above, it is typically assumed that the output at an image plane of an optical system is given as:

Output=Input+System    (6)

This assumes that the input and the system errors or aberrations may be independently assessed, and that, accordingly, there is no "cross-talk" among the input, system, and pupil diffraction. However, the inventors have found that such cross-talk can exist. For example, aberrations in the term "Input" in Equation (6) may affect the magnitude of the term "System" In such embodiment, the output may be calculated, for example, according to the relation:

Output=Input+System+Input*System    (6')

If either Input or System errors are zero or very close to zero, then the cross-term, Input*System, is zero, Equation (6) is valid.

The inventor have found that in cases where either the input or the system have no error or aberrations, there is no cross-talk and the above relationship is valid. However, the inventors have also found that in some situations, cross-talk can actually have a significant affect on the output, particularly in terms of higher order aberration (e.g., above 4th order). Accordingly, a more accurate assessment of the output may be provided by:

Output=Input+System Error+$f$(input, system)+$g$(input, pupil)+$h$(system, pupil)    (7)

Accordingly, the following effort functions were defined:

Error Function 1=Output−Input    (8)

Error Function 2=(output−input−system error)/input    Referring to Equations (9)

Referring to Equations (3) through (5) above, the inventors used Fresnel-Kirchhoff's approximate formula to provide a more accurate analysis of an optical imaging system output that accounts for cross-talk. The need for such an approach has been illustrated by the inventors using the following method 200:

1. At input plane, provide values in Zernike coefficients.
2. At lens 42 and lens 45 (see FIG. 2), input aberrations (e.g., 0.1 microns spherical aberration)
3. Using a ray tracing program, decenter lens 42 relative to lens 45 (e.g., 0.1 mm to 0.5 mm) and introduce relative tilt (2 to 5 degrees) and defocused (e.g., 0.1 mm);
4. Calculate the wavefront at an output plane by wavefront maps and Zernike coefficients;
5. Calculate an error function using the wavefront maps and fit to Zernike polynomials.
6. Repeat 1-5 with lens 42 shifted left by 10 mm.
7. Repeat 1-5 with zero input (2) OR zero system error (zero all in 4) will make the error function 2 zero.

Figure 2:
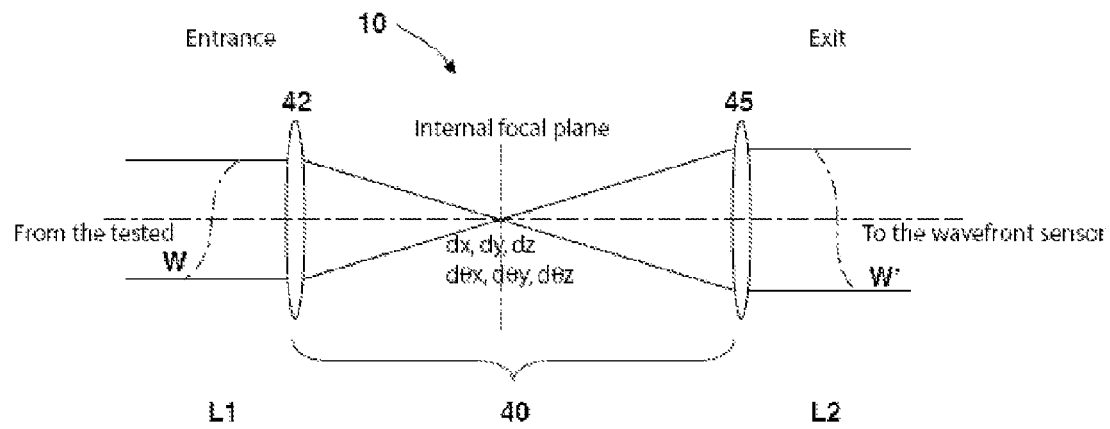
FIG. 2 is a schematic drawing of the image or wavefront transfer system for the wavefront sensor shown in FIG. 1.

Accordingly, and by way of example, the relay system shown in FIG. 2 was used to demonstrate the effects of cross-talk in producing significant output error. It will be appreciated that this specific example is not meant to limit the scope of the present invention, but is give as a way of demonstrating the importance of using an analysis according to embodiments of the present invention in the design of optical systems, for example in the field of ophthalmic diagnostic.

In steps 1-3 of method 200 above, various errors are introduced into the input and system shown in FIG. 2. Input errors are shown in terms of Zernike coefficients in the second column of TABLE 1 below. The column labeled "OUTPUT" in TABLE 1 shows the resulting output after the system errors are subtracted out. Thus, the error in percent introduced by cross-talk is shown in the column in TABLE 1 labeled "Error Function 2". As can be seen, these errors are significant for many of the Zernike terms. In TABLE 2, an additional error is introduce by way of displacement of the object plan by 10 millimeters. This amount of displacement error is typical in aberrometers used to measure aberrations of a subjects eye or cornea.

TABLE 1

| INPUT | CONJUGATED | OUTPUT | Error Function 2 |
|---|---|---|---|
| Z 1 | 0.73:1 | 1.185371 | |
| Z 2 | −0.10:4^(1/2) (p) * COS (A) | −0.100265 | |
| Z 3 | −0.10:4^(1/2) (p) * SIN (A) | −0.309667 | |
| Z 4 | 0.32:3^(1/2) (2p^2 − 1) | 0.331621 | 1.95% |
| Z 5 | −0.10:6^(1/2) (p^2) * SIN (2A) | −0.095975 | −4.02% |
| Z 6 | −0.10:6^(1/2) (p^2) * COS (2A) | −0.096498 | −3.50% |
| Z 7 | −0.10:8^(1/2) (3p^3 − 2p) * SIN (A) | −0.094691 | −5.31% |
| Z 8 | −0.10:8^(1/2) (3p^3 − 2p) * COS (A) | −0.093219 | −6.78% |
| Z 9 | −0.10:8^(1/2) (p^3) * SIN (3A) | −0.095711 | −4.29% |
| Z 10 | −0.10:8^(1/2) (p^3) * COS (3A) | −0.097180 | −2.82% |
| Z 11 | −0.10:5^(1/2) (6p^4 − 6p^2 + 1) | −0.288831 | −6.76% |
| Z 12 | −0.05:10^(1/2) (4p^4 − 3p^2) * COS (2A) | −0.046635 | −6.73% |
| Z 13 | −0.05:10^(1/2) (4p^4 − 3p^2) * SIN (2A) | −0.046091 | −7.82% |
| Z 14 | −0.05:10^(1/2) (p^4) * COS (4A) | −0.048774 | −2.45% |
| Z 15 | −0.05:10^(1/2) (p^4) * SIN (4A) | −0.046940 | −6.12% |
| Z 16 | −0.05:12^(1/2) (10p^5 − 12p^3 + 3p) * COS (A) | −0.043968 | −12.06% |
| Z 17 | −0.03:12^(1/2) (10p^5 − 12p^3 + 3p) * SIN (A) | −0.024911 | −16.96% |
| Z 18 | −0.03:12^(1/2) (5p^5 − 4p^3) * COS (3A) | −0.027555 | −8.15% |

TABLE 1-continued

| INPUT | CONJUGATED | OUTPUT | Error Function 2 |
|---|---|---|---|
| Z 19 | $-0.03{:}12^{(1/2)} (5p^5 - 4p^3) * SIN (3A)$ | $-0.026558$ | $-11.47\%$ |
| Z 20 | $-0.03{:}12^{(1/2)} (p^5) * COS (5A)$ | $-0.028616$ | $-4.61\%$ |
| Z 21 | $-0.03{:}12^{(1/2)} (p^5) * SIN (5A)$ | $-0.027833$ | $-7.22\%$ |
| Z 22 | $-0.03{:}7^{(1/2)} (20p^6 - 30p^4 + 12p^2 - 1)$ | $-0.021155$ | $-21.67\%$ |
| Z 23 | $-0.01{:}14^{(1/2)}A$ | $-0.007083$ | $-29.17\%$ |
| Z 24 | $-0.01{:}14^{(1/2)}A$ | $-0.007631$ | $-23.69\%$ |
| Z 25 | $-0.01{:}14^{(1/2)} (6p^6 - 5p^4) * SIN (4A)$ | $-0.008299$ | $-17.01\%$ |
| Z 26 | $-0.01{:}14^{(1/2)} (6p^6 - 5p^4) * COS (4A)$ | $-0.009175$ | $-8.25\%$ |
| Z 27 | $-0.01{:}14^{(1/2)} (p^6) * SIN (6A)$ | $-0.008496$ | $-15.04\%$ |
| Z 28 | $-0.01{:}14^{(1/2)} (p^6) * COS (A)$ | $-0.009279$ | $-7.21\%$ |
| Z 29 | $-0.01{:}16^{(1/2)} SIN (A)$ | $-0.005762$ | $-42.38\%$ |
| Z 30 | $-0.01{:}16^{(1/2)} COS (A)$ | $-0.005568$ | $-44.32\%$ |
| Z 31 | $-0.01{:}16^{(1/2)}3A$ | $-0.007889$ | $-21.11\%$ |
| Z 32 | $-0.01{:}16^{(1/2)}3A$ | $-0.008411$ | $-15.89\%$ |
| Z 33 | $-0.01{:}16^{(1/2)} (7p^7 - 6p^5) * SIN (5A)$ | $-0.009393$ | $-6.07\%$ |
| Z 34 | $-0.01{:}16^{(1/2)} (7p^7 - 6p^5) * COS (5A)$ | $-0.008911$ | $-10.89\%$ |
| Z 35 | $-0.01{:}16^{(1/2)} (p^7) * SIN (7A)$ | $-0.009280$ | $-7.20\%$ |
| Z 36 | $-0.01{:}16^{(1/2)} (p^7) * COS (7A)$ | $-0.009105$ | $-8.95\%$ |
| Z 37 | $-0.01{:}9^{(1/2)} + 1)$ | $-0.004645$ | $-52.83\%$ |

TABLE 2

| INPUT | NON-CONJUGATED +10 mm | OUTPUT | Error Function 2 |
|---|---|---|---|
| Z 1 | 0.73:1 | 1.188192 | |
| Z 2 | $-0.10{:}4^{(1/2)} (p) * COS (A)$ | $-0.099986$ | |
| Z 3 | $-0.10{:}4^{(1/2)} (p) * SIN (A)$ | $-0.308426$ | |
| Z 4 | $0.32{:}3^{(1/2)} (2p^2 - 1)$ | $0.334590$ | $2.88\%$ |
| Z 5 | $-0.10{:}6^{(1/2)} (p^2) * SIN (2A)$ | $-0.095868$ | $-4.13\%$ |
| Z 6 | $-0.10{:}6^{(1/2)} (p^2) * COS (2A)$ | $-0.096638$ | $-3.36\%$ |
| Z 7 | $-0.10{:}8^{(1/2)} (3p^3 - 2p) * SIN (A)$ | $-0.093921$ | $-6.08\%$ |
| Z 8 | $-0.10{:}8^{(1/2)} (3p^3 - 2p) * COS (A)$ | $-0.093020$ | $-6.98\%$ |
| Z 9 | $-0.10{:}8^{(1/2)} (p^3) * SIN (3A)$ | $-0.096921$ | $-4.08\%$ |
| Z 10 | $-0.10{:}8^{(1/2)} (p^3) * COS (3A)$ | $-0.097297$ | $-2.70\%$ |
| Z 11 | $-0.10{:}5^{(1/2)} (6p^4 - 6p^2 + 1)$ | $-0.286254$ | $-9.33\%$ |
| Z 12 | $-0.06{:}10^{(1/2)} (4p^4 - 3p^2) * COS (2A)$ | $-0.046927$ | $-6.15\%$ |
| Z 13 | $-0.06{:}10^{(1/2)} (4p^4 - 3p^2) * SIN (2A)$ | $-0.046072$ | $-7.86\%$ |
| Z 14 | $-0.06{:}10^{(1/2)} (p^4) * COS (4A)$ | $-0.048841$ | $-2.32\%$ |
| Z 15 | $-0.06{:}10^{(1/2)} (p^4) * SIN (4A)$ | $-0.047399$ | $-5.20\%$ |
| Z 16 | $-0.06{:}12^{(1/2)} (10p^5 - 12p^3 + 3p) * COS (A)$ | $-0.043978$ | $-12.04\%$ |
| Z 17 | $-0.03{:}12^{(1/2)} (10p^5 - 12p^3 + 3p) * SIN (A)$ | $-0.024479$ | $-18.40\%$ |
| Z 18 | $-0.03{:}12^{(1/2)} (5p^5 - 4p^3) * COS (3A)$ | $-0.027777$ | $-7.41\%$ |
| Z 19 | $-0.03{:}12^{(1/2)} (5p^5 - 4p^3) * SIN (3A)$ | $-0.026923$ | $-10.26\%$ |
| Z 20 | $-0.03{:}12^{(1/2)} (p^5) * COS (5A)$ | $-0.028486$ | $-5.05\%$ |
| Z 21 | $-0.03{:}12^{(1/2)} (p^5) * SIN (5A)$ | $-0.028431$ | $-5.23\%$ |
| Z 22 | $-0.03{:}7^{(1/2)} (20p^6 - 30p^4 + 12p^2 - 1)$ | $-0.019803$ | $-26.17\%$ |
| Z 23 | $-0.01{:}14^{(1/2)}A$ | $-0.007201$ | $-27.99\%$ |
| Z 24 | $-0.01{:}14^{(1/2)}A$ | $-0.008088$ | $-19.12\%$ |
| Z 25 | $-0.01{:}14^{(1/2)} (6p^6 - 5p^4) * SIN (4A)$ | $-0.008896$ | $-11.04\%$ |
| Z 26 | $-0.01{:}14^{(1/2)} (6p^6 - 5p^4) * COS (4A)$ | $-0.009299$ | $-7.01\%$ |
| Z 27 | $-0.01{:}14^{(1/2)} (p^6) * SIN (6A)$ | $-0.009083$ | $-9.17\%$ |
| Z 28 | $-0.01{:}14^{(1/2)} (p^6) * COS (6A)$ | $-0.009026$ | $-9.74\%$ |
| Z 29 | $-0.01{:}16^{(1/2)} SIN (A)$ | $-0.005442$ | $-45.58\%$ |

TABLE 2-continued

| INPUT | NON-CONJUGATED +10 mm | OUTPUT | Error Function 2 |
|---|---|---|---|
| Z 30 | $-0.01:16\hat{}(1/2) \cos(A)$ | $-0.005801$ | $-41.99\%$ |
| Z 31 | $-0.01:16\hat{}(1/2)3A)$ | $-0.008378$ | $-16.22\%$ |
| Z 32 | $-0.01:16\hat{}(1/2)3A)$ | $-0.008716$ | $-12.84\%$ |
| Z 33 | $-0.01:16\hat{}(1/2) (7p\hat{}7 - 6p\hat{}5) * \sin(5A)$ | $-0.010059$ | $0.59\%$ |
| Z 34 | $-0.01:16\hat{}(1/2) (7p\hat{}7 - 6p\hat{}5) * \cos(5A)$ | $-0.008808$ | $-11.92\%$ |
| Z 35 | $-0.01:16\hat{}(1/2) (p\hat{}7) * \sin(7A)$ | $-0.009793$ | $-2.07\%$ |
| Z 36 | $-0.01:16\hat{}(1/2) (p\hat{}7) * \cos(7A)$ | $-0.008750$ | $-12.50\%$ |
| Z 37 | $-0.01:9\hat{}(1/2) +1)$ | $-0.004604$ | $-53.24\%$ |

By way of summary, it was concluded that:
1. A real relay system can introduce an input-dependent error due to the crosstalk between the input, the system, and the pupil diffraction to the output wavefront
2. Error could be introduced if the measured wavefront plane is not conjugated to the pupil plane because of changes in the wavefront during propagation
3. The quality of the relay optics and the alignment of the relay system are critical.
4. Errors measuring lower order aberrations of the input wavefront may be relatively low, while those of higher order aberrations may be relatively high, as summarized in the following table:

| Not ignorable | 1 | 2 (system RMS < λ/4) |
|---|---|---|
| Low order (up to 4th order) | Determined by the system | Up to 5% |
| High order (above 4th order) | Determined by the system | Up to 50% |

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiments disclosed. On the contrary, the intention is to cover modifications and alternate constructions coming within the spirit and scope of the invention as generally expressed by the following claims, which particularly point out and distinctly claim the subject matter of the invention.

What is claimed is:

1. A system for providing vision, comprising:
   an aberrometer configured to measure a received wavefront, the aberrometer including:
   a sensor configured to detect the received wavefront; and
   a transfer optical system for transferring an input wavefront so as to provide the received wavefront at or near the wavefront sensor; and
   a processor in communication with the aberrometer, the processor configured to determine at least one aberration of the received wavefront and calculate the input wavefront based on the received wavefront and one or more system error parameters, the one or more system error parameters being calculated based on one or more input parameters selected from the group consisting of aberrations of the transfer optical system and misalignment of one or more components of the aberrometer.

2. The system of claim 1, wherein input wavefront is disposed at a pupil of a subject eye.

3. The system of claim 1, wherein the system error is represented by a polynomial equation.

4. The system of claim 3, wherein polynomial equation includes a plurality of coefficients, the coefficients being Zernike coefficients or Fourier coefficients.

5. The system of claim 1, wherein the input wavefront depends on a cross-term of the input wavefront and the one or more system error parameters.

6. The system of claim 1, wherein the aberrometer further comprises:
   an illumination source;
   an illuminating optical system for directing light from the illumination source to the subject eye to create an input wavefront from light reflected by the subject eye.

7. The system of claim 6, wherein wavefront sensor comprises detector and a plurality of lenslet for receiving the received wavefront and focusing light from the received wavefront onto the detector.

8. The system of claim 1, wherein the system error parameters are based on Fresnel-Kirchhoff's approximate formula.

9. The system of claim 1, wherein the system further comprises an ablation system configured to modify a cornea of the subject eye based on the received wavefront and the one or more system error parameters.

10. A method of wavefront processing for providing vision, the method comprising the steps of:
   providing an input wavefront located at an input plane;
   detecting a received wavefront with an aberrometer, the aberrometer comprising a wavefront sensor, a transfer optical system, and one or more system error parameters, the one or more system error parameters based on one or more input parameters selected from the group consisting of aberrations of the transfer optical system and misalignment of one or more components of the aberrometer;
   transferring the input wavefront with the transfer optical system so as to provide the received wavefront at or near the wavefront sensor;
   calculating the input wavefront based on the received wavefront and the one or more system error parameters; and
   determining at least one aberration of the received wavefront.

* * * * *